(12) United States Patent
Archibald et al.

(10) Patent No.: US 8,034,800 B2
(45) Date of Patent: Oct. 11, 2011

(54) ANTIVIRAL MACROCYCLE DERIVATIVES AND METAL COMPLEXES, INCORPORATING BRIDGED MACROCYCLES

(75) Inventors: Stephen James Archibald, York (GB); Elizabeth Amie Lewis, Hull (GB); Timothy J. Hubin, Weatherford, OK (US)

(73) Assignee: University of Hull (GB)

( * ) Notice: Subject to any disclaimer, the term of this patent is extended or adjusted under 35 U.S.C. 154(b) by 836 days.

(21) Appl. No.: 11/629,035

(22) PCT Filed: Jun. 10, 2005

(86) PCT No.: PCT/GB2005/002297
§ 371 (c)(1),
(2), (4) Date: Mar. 11, 2008

(87) PCT Pub. No.: WO2005/121109
PCT Pub. Date: Dec. 22, 2005

(65) Prior Publication Data
US 2008/0267866 A1   Oct. 30, 2008

(30) Foreign Application Priority Data

Jun. 10, 2004   (GB) .................................. 0412893.0

(51) Int. Cl.
*A61K 31/33*       (2006.01)
*C07D 257/00*      (2006.01)
(52) U.S. Cl. .................. 514/183; 540/473; 540/474
(58) Field of Classification Search .................. None
See application file for complete search history.

(56) References Cited

U.S. PATENT DOCUMENTS 5,047,527 A   9/1991   Handel et al.
5,997,353 A   12/1999   Guiol

FOREIGN PATENT DOCUMENTS

| EP | 0870768 | 10/1998 |
|---|---|---|
| JP | 2000-239272 | 9/2000 |
| WO | 98/39335 | 9/1998 |
| WO | WO 98/39098 | 9/1998 |
| WO | 02/26267 | 4/2002 |

OTHER PUBLICATIONS

Xu et al. Chemical Research and Toxicology, 1998, 11, pp. 247-251.*
Jantzen and Robinson Modern Pharmaceutics, 1996, p. 596.*
Orvedahl et al. Cell Death and Differentiation, 2009, 16, 57-69.*
Liang, Xiangyang, et al., "Structure and Dynamics of Metallomacrocycles: Recognition of Zinc Xylyl-Bicyclam by an HIV Coreceptor," J. Am. Chem. Soc. 2002, vol. 124, pp. 9105-9112.
Liang, Xiangyang, et al., "Cadmium Cyclam Complexes: Interconversion of Cis and Trans Configurations and Fixationof $CO_2$," Inorg. Chem 2002, vol. 41, pp. 4539-4547.

Hu, Chuanjiang, et al., "Solution-State and Solid-State Structural Characterization of Complexes of a New Macrocyclic Ligand Containing the 1,5-Diazacyclooctane Subunit," Inorg. Chem. 2003, vol. 42, pp. 742-749.
Rosenkilde, Mette M., et al., "Molecular Mechanism of AMD3100 Antagonism in the CXCR4 Receptor," The Journal of Biological Chemistry, Jan. 23, 2004, vol. 279, No. 4, pp. 3033-3041.

(Continued)

*Primary Examiner* — Noble Jarrell
(74) *Attorney, Agent, or Firm* — Harness, Dickey & Pierce, P.L.C.

(57) ABSTRACT

A compound of Formulae (1), (2) or (3), $A_1$-Ph (1) or $A_1$-Ar-$A_2$ (2) or $A_1$-$(A_2)$A'-$A_3$ (3) wherein $A_1$, $A_2$ and $A_3$ are selected from Formulae 4, 5 and 6:

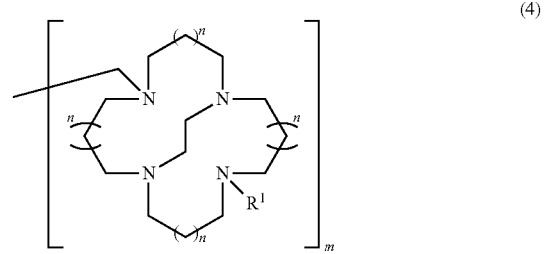

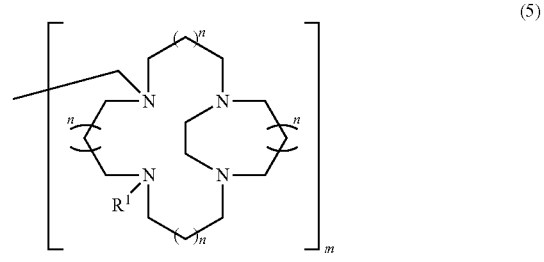

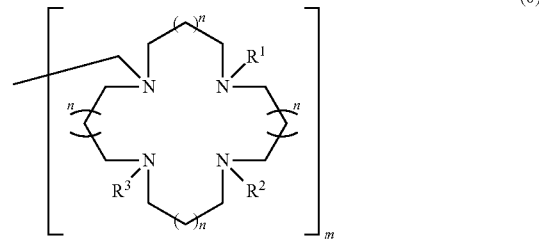

or a salt whereof; wherein Ar is selected from the group consisting of 1,2-phenyl, 1,3-phenyl and 1,4-phenyl optionally substituted with one or more methyl groups; m and n are independently integers from 0 to 1; Ph is phenyl, optionally substituted with one or more methyl groups; $Ar^1$ is trisubstituted phenyl optionally substituted with one or more phenyl groups; and $R^1$, $R^2$ and $R^3$ are independently selected from the group consisting of H, Me and linear chain $C_2$-$C_4$ alkyl.

11 Claims, 1 Drawing Sheet

OTHER PUBLICATIONS

Achmatowicz, Michal, et al., "Direct Synthesis of 1,1'[1,4-Phenylenebis(methylene)]-bis-1,4,8,11-tetraazacyclotetradecane Octahydrochloride (AMD 3100) without the Use of Protecting Groups," J. Org. Chem. 2003, vol. 68, pp. 6435-6436.

Lebon, Bertrand, et al., "AMD3100 Conjugates as Components of Targeted Nonviral Gene Delivery Systems: Synthesis and in Vitro Transfection Efficiency of CXCR4-Expressing Cells," Bioconjugate Chem. 2004, vol. 15, pp. 413-423.

Siegfried, Liselotte, et al., "Tren centered tris-macrocycles as polytopic ligands for CU(II) and NI(II)," The Royal Society of Chemistry 2004, pp. 2115-2124.

Princen, Katrien, et al., "Establishment of a novel CCR5 and CXCR4 expressing CD4+ cell line which is highly sensitive to HIV and suitable for high-throughput evaluation of CCR5 and CXCR4 antagonists," Retrovirology 2004, Mar. 8, 2004, 1:2.

Jekle Anreas, et al. "In Vivo Evolution of Human Immunodeficiency Virus Type 1 toward Increased Pathogenicity through CXCR4-Mediated Killing of Uninfected CD4 T Cells," Journal of Virology, May 2003, pp. 5846-5854.

Hatse, Sigrid, et al., "Mutations at the CXCR4 interaction sites for AMD3100 influence anti-CXCR4 antibody binding and HIV-1 entry," FEBS Letters 546 (2003), pp. 300-306.

Declercq, Erik, "New developments in anti-HIV chemotherapy," Biochimica et Biophysica Acta 1587 (2002) pp. 258-275.

Hatse, Sigrid, et al., "Mutation of Asp171 and Asp262 of the Chemokine Receptor CXCR4 Impairs Its Coreceptor Function for Human Immunodeificiency Virus-1 Entry and Abrogates the Antagonistic Activity of AMD3100," Molecular Pharmacology 2001, vol. 60, pp. 164-173.

Hatse, Sigrid, et. al., "Chemokine receptor inhibition by AMD3100 is strictly confined to CXCR4," FEBS Letters 527 (2002), pp. 255-262.

Lukacs, Nicholas W., et al., "AMD3100, a CxCR4 Antagonist, Attenuates Allergic Lung Inflammation and Airway Hyperreactivity," American Journal of Pathology, Apr. 2002 vol. 160, No. 4, pp. 1353-1360.

Blanco, Julia, et al., "The CXCR4 Antagonist AMD3100 Efficiently Inhibits Cell-Surface-Expressed Human Immunodeficiency Virus Type 1 Envelope-Induced Apoptosis," Antimicrobial Agents and Chemotherapy, Jan. 2000, pp. 51-56.

Bridger, Gary J., et. al, "A Versitile Intermediate for the Preparation of C-Functionalized Azamacroryeles and Application to the Synthesis of the Potent Anti-HIV Agent (±)JM2936," J. Org. Chem. 1996, vol. 61, pp. 1519-1522.

Labrosse, Beatrice, et al., "Determinants for Sensitivity of Human Immunodeficiency Virus Coreceptor CXCR4 to the Blcyclam AMD3100," Journal of Virology, Aug. 1998, pp. 6381-6388.

Declercq, Erik, et al., "Potent and selective unhibition of human immunodeficiency virus (HIV)-1 and HIV-2 replication by a class of bicyclams interacting with a viral uncoating event," Proc. Natl. Acad. Sci., Jun. 1992, vol. 89, pp. 5286-5290.

Weisman, Gary R., et al., "Cross-Bridged Cyclam. Pronation and Li+ Complextion in a Diamond-Lattice Cleft," J. Am. Chem. Soc. 1990, vol. 112, pp. 8604-8605.

Rubin, Joshua B., et al., "A small-molecule antagonist of CXCR4 inhibits intracranial growth of primary brain tumors," PNAS, Nov. 11, 2003, vol. 100, No. 23, pp. 13513-13518.

Scotton, Chris J., et al., "Multiple Actions of the Chemokine CXCL12 on Epithelial Tumor Cells in Human Ovarian Cancer," Cancer research, Oct. 15, 2002, vol. 62, pp. 5930-5938.

Mochizuki, Katsura, et al., "Synthesis and Structure of [6,6'-Bi(5,7-demethyl-1,4,8,11-tetraazacyclotetradecane]dinickel(II) Triflate and Its Catalytic Activity for Photochemical $CO_2$ Reduction," Inorg. Chem. 1996, vol. 35, pp. 5132-5136.

Liang, Xiangyang, et al., "Selective Recognition of Configurational Substates of Zinc Cyclam by Carboxylates: Implications for the Design and Mechanism of Action of Anti-HIV Agents," Chem. Eur. J. 2003, vol. 9, pp. 4709-4717.

Niu, Weijun, et al., Gallium(III) and indium(III) complexes of cross-bridged tetraamine ligands, Inorganic Chemistry Communications 2002, vol. 5, pp. 1-4.

Niu, Weijun, et al., Copper(II) and zinc(II) complexes of amide pendant-armed cross-bridged tetraamine ligands, Polyhedron 2004, vol. 23, pp. 1019-1025.

Hunter, Tina M., et al., "Configurations of metallocyclams and revelance to anti-HIV activity" Journal of Inorganic Biochemistry 2004, vol. 98, pp. 713-719.

Liang, Xiangyang, et al., "Cyclam complexes and their applications in medicine," Chem. Soc. Rev. 2004, vol. 33, pp. 246-266.

Gaudinet-Hamann, Beatrice, et al., "A Convenient Synthesis of Bis-Tetraazamacrocycles," Tetrehedron Letters 1999, vol. 40, pp. 287-290.

Niu, Weijun, et al., "Two novel zinc(II) complexes of the 1,8-cross-bridged cyclam ligand and their structures," Inorganic Chemistry Communications 2 (1999), pp. 361-363.

Fabbrizzi, Luigi, et al., "pH-Controlled Florescent Emission in the Nickel(II) Complex of a Biofunctional Tetramine Macrocycle," Inorganic Chemistry 2002, vol. 41, pp. 4612-4614.

Ciampolini, Mario, et al., "Dinickel and Dicopper Complexes with N,N-Linked Bis(cyclam) Ligands. An ideal System for the Investigation of Electrostatic Effects on the Redox Behavior of Pairs of Metal Ions," Inorg. Chem. 1987, vol. 26, pp. 3527-3533.

Pattrick, Gary, et al., "A Crystallographic Study of a Red and a Blue Complex of Copper(II) formed with Different Geometric Isomers of a Reinforced Macrocycle," J. Chem. Soc. Dalton Trans. 1991, pp. 1295-1299.

Paisey, Stephen J., et al., "Anti-viral cyclam macrocycles: rapid zinc uptake at physiological pH," Chem. Commun. 2004, pp. 306-307.

Hancock, Robert D., et al., "Structurally reinforced macrocyclic ligands," Pure & Appl. Chem. 1993, vol. 65, No. 3, pp. 473-476.

Kang, Shin-Geol, et al., "Synthesis and characterization of new adjacent-bridged tetraaza macrocyclic compounds with C-alkyl groups: crystal structure and spectral properties of a copper(II) complex," Inorganica Chimica Acta 2004, vol. 357, pp. 2783-2790.

Wright-Garcia, Kimberley, et al., "Effects of Steric Constraint on Chromium(III) Complexes of Tetraazamacrocycles. Chemistry and Excited-State Behavior of 1,4-C2-Cyclam Complexes," Inorg. Chem. 2003, vol. 42, pp. 4885-4890.

Xu, Daqiang, et al., "An Expeditious Synthesis of a Biscyclam with an Aromatic Linker," Tetrahedron Letters 1996, vol. 37, No. 30, pp. 5301-5304.

Wainwright, Kevin P., "Bridging Alkylation of Saturated Polyaza Macrocycles: A Means for Imparting Structural Rigidity," Inorg. Chem. 1980, vol. 19, pp. 1396-1398.

Roignant, et al., Database accession No. 7211737, (XP-002357028—BRN), J. Chem. Soc. Chem. Commun. 1995, vol. 12, pp. 1233-1234.

Yoo, Jeongso, et al., Database accession No. 9349922, (XP-002357029—BRN), Chem. Commun. 2003, vol. 6, pp. 766-767.

Kotek, et al., Database accession No. 8571265, (XP-002357030—BRN), Collect. Czech. Chem. Commun. 2000, vol. 65, No. 2, pp. 234-266.

International Search Report and Written Opinion of the International Searching Authority, mailed Dec. 21, 2005; ISA/EP.

Search Report for GB 0412893.1, date of search Oct. 18, 2004.

"Activity of Different Bicyclam Derivatives against Human Immunodeficiency Virus Depends on Their Interaction with the CXCR4 Chemokine Receptor", by José A. Esté, Cecilia Cabrera, Erik DeCercq, Sofie Struyf, Jo Van Damme, Gary Bridger, Renato T. Skerlj, Michael J. Abrams, Geoffrey Henson, Arantxa Gutierrez, Bonaventura Clotet, and Dominque Schols; The American Society for Pharamcology and Experimental Therapeutics, Molecular Pharmacology, 55:67-73 (1999).

"Bicyclams, Selective Antagonists of the Human Chemokine Receptor CXCR4, Potently Inhibit Feline Immunodeficiency Virus Replication", by Herman F. Egberink, Erik DeClercq, Arno L. W. Van Vliet, Jan Balzarini, Gary J. Bridger, Geoffrey Henson, Marian C. Horzinek, and Dominque Schols; Journal of Virology, vol. 73, No. 8, Aug. 1999, pp. 6346-6352.

"Metal Ion Enhanced Binding of AMD3100 to Asp262 in the CXCR4 Receptor", by Lars Ole Gerlach, Janus S. Jakobsen, Kasper P. Jensen, Mette R. Rosenkilde, Renato T. Skerlj, Ulf Ryde, Gary J. Bridger, and Thue W. Schwartz; American Chemical Society, Biochemistry 2003, 42, 710-717.

"Molecular Interactions of Cyclam and Bicyclam Non-peptide Antagonists with the CXCR4 Chemokine Receptor", by Lars Ole Gerlach, Renato T. Skerlj, Gary J. Bridger, and Thue W. Schwartz; The Journal of Biological Chemistry, vol. 276, No. 17, Issue of Apr. 27, 2001, pp. 14153-14160.

"Quantitative Structural Activity Relationship Study of Bis-Tetraazacyclic Compounds. A Novel Series of HIV-1 and HIV-2 Inhibitors", by Heidi C Joso, Karen deVreese, Rudi Pauwels, Erik DeClercq, Geoff W. Henson, and Gary J. Bridger; American Chemical Society, Journal of Medicinal Chemistry 1995, vol. 38, No. 19, pp. 3865-3873.

"Synthesis and Structure—Activity Relationships of Phenylenebis(methylene)-Linked Bis-tetraazamacrocycles That Inhibit Human Immunodeficiency Virus Replication. 2. Effect of Heteroaromatic Linkers on the Activity of Bicyclams", by Gary J. Bridger, Renato T. Skerlj, Sreenivasan Padmanabhan, Stephen A. Martellucci, Geoffrey W. Henson, Michael J. Abrams, Heidi C. Joso, Myriam Witvrouw, Karen DeVreese, Rudi Pauwels, and Erik DeClercq; American Chemical Society, Journal of Medicinal Chemistry 1996, vol. 39, No. 1, pp. 109-119.

"The bicyclam AMD3100 story"; by Erik DeClercq; Nature Reviews, Drug Discovery, vol. 2, Jul. 2003, pp. 581, 583, 585 and 587.

* cited by examiner

ANTIVIRAL MACROCYCLE DERIVATIVES AND METAL COMPLEXES, INCORPORATING BRIDGED MACROCYCLES

FIELD OF THE INVENTION

This invention relates to novel mono -or poly-azamacrocycle derivatives incorporating bridged macrocycles, methods of production thereof and dosage forms incorporating these derivatives. The invention also relates to use of the derivatives for manufacture of medicaments and to a method of treatment using these dosage forms. Preferred compounds in accordance with this invention are useful as CXCR4 co-receptor antagonists, especially for anti-HIV and other antiviral treatments.

BACKGROUND OF THE INVENTION

CXCR4 chemokine receptors, are found on the surface of immune cells, and interact with the specific natural ligand, known as CXCL12 or stromal cell-derived factor 1α (SDF-1α). They have been revealed to play a role in a number of disease states. For example the CXCR4 SDF-1α system has involvement in cancer progression and metastasis, and in the development of rheumatoid arthritis. CXCR4 and CCR5 co-receptors have been identified as the entry route for HIV into cells, providing a new therapeutic approach to treatment by entry inhibitor drugs rather than the current preference for reverse transcriptase and protease inhibitors. An object of the present invention is to provide new antagonists for the CXCR4 co-receptor.

This invention may provide novel compounds that selectively bind to chemokine receptors based on cross bridged macrocycles. The compounds may incorporate metal ions and form stable complexes prior to administration.

It is an object of this invention to provide examples of bridged azamacrocyclic derivatives that show specific chemokine receptor binding.

SUMMARY OF THE INVENTION

According to a first aspect of the present invention there is provided compound of Formulae 1, 2 or 3, (1)

or

(2)

or (3)

wherein $A_1$, $A_2$ and $A_3$ are selected from Formulae 4, 5 and 6:

(4)

(5)

(6)

or a salt whereof;

wherein Ar is selected from the group consisting of 1,2-phenyl, 1,3-phenyl and 1,4-phenyl optionally substituted with one or more methyl groups;

m and n are independently integers from 0 to 1;

Ph is phenyl optionally functionalised with one or more groups $R^4$, wherein $R^4$ is selected from the group consisting of: methyl, other $C_1$-$C_4$ alkyl and fluorophoRes;

Ar' is trisubstituted phenyl optionally substituted with one or more phenyl groups; and

$R^1$, $R^2$ and $R^3$ are independently selected from the group consisting of H, Me and linear chain $C_2$-$C_4$ alkyl;

with the provisos that when Ph is unsubstituted phenyl in Formula 1 and $A_1$ is Formula (4), $R_1$ is not Me; and wherein not more than one of $A_1$ and $A_2$ in Formula (2) or no more than two of $A_1$, $A_2$ and $A_3$ in Formula (3) is Formula (6).

The invention further provides a complex of a compound selected from Formulae 1, 2 or 3 with a metal ion selected from the group consisting of: transition elements and mixtures thereof. In preferred compounds the complex is formed with divalent ions of copper and zinc or a mixture thereof.

In preferred compounds of Formula 1, 2 or 3, $A_1$ and $A_2$ are different. In this case the compound is termed 'unsymmetrical'. In particularly preferred compounds $A_1$, $A_2$ and $A_3$ will be represented by Formulae 7 to 15.

(7)

(8)

(9)

(10)

(11)

(12)

(13)

(14)

(15)

In particularly preferred compounds one or both of R is H or Me.

Preferred compounds may be selected from Formulae 16 to 23:

(16)

(17)

(18)

(19)

(20)

(21)

(22)

(23)

Preferred compounds of the present invention may bind to CXCR4 chemokine cell surface receptors and find particular but not exclusive application as CXCR4 co-receptor antagonists which are useful in anti-viral treatment, particularly HIV treatment.

In another aspect this invention provides a method for treating a viral disease in a mammal comprising administering to said mammal an effective amount of a compound of Formula 1, 2 or 3, or a pharmaceutically acceptable salt or pro-drug thereof. Compounds of the present invention for application for comparative human and of veterinary treatments.

In another aspect this invention provides a pharmaceutical composition comprising a compound of Formula 1, 2 or 3 and a pharmaceutically inert carrier.

In another aspect such compounds may be labelled with radioactive metal isotopes or fluorescent tags allowing in vitro or in vivo imagine of the chemokine receptors for diagnostic or therapeutic use. Such compounds may also be used in the screening of drugs for chemokine receptor binding.

Compounds of the present invention find application in manufacture of imaging agents, for example by covalently binding, chelating or coupling to a fluorophore or radioisotope. A $^{64}Cu$ compound may be used. A fluorophore or radioisotope containing moiety may be linked to the compound by covalent substitution to the phenyl group, aryl group or to the macrocycle. Such imaging agents may be used for drug screening for either CXCR4 binding molecules or for chemokine receptor imaging from cellular level to diagnostic imaging of whole organisms.

The invention is further described by means of example but not in any limitative sense.

Compounds of the present invention are prepared from readily available starting materials.

DRAWINGS

The drawings described herein are for illustration purposes only of selected embodiments and are not intended to limit the scope of the present disclosure in any way.

DETAILED DESCRIPTION OF THE INVENTION

The present invention relates to mono- or poly-azamacrocyclic complexes that incorporate a bridged macrocycle. A further aspect of the invention is the transition metal complexes that can be formed wherein said transition metal may have a valence of +1, +2, +3, +4 or +5. In certain aspects of the invention one or more different transition metals may be incorporated. The macrocyclic compounds or the metal complexes of the present invention are suitable for use as pharmaceuticals that specifically bind to chemokine receptors.

One aspect of the present invention relates to the blocking of a chemokine receptor by binding with a compound of the invention and the subsequent disruption of the chemokine in another role.

In a preferred embodiment one bridged macrocyclic ring ($A_1$), of the type shown in the non-limiting examples of Formulae 7 to 15, is attached to the aryl ring, Formula 1.

In a further preferred embodiment three macrocyclic rings, with one or more of the type shown in the non-limiting examples of Formulae 7 to 15, are attached to the aryl ring, Formula 3.

In the most preferred embodiment two macrocyclic rings are attached to the aryl ring, with one or more from the non-limiting examples of Formulae 7 to 15, giving the preferred compounds shown of Formula 16 to 23.

In a preferred embodiment the two carbon linker of at least one macrocycle connects two non-adjacent nitrogens within the ring:

In this embodiment n is 0 or 1 and R is an alkyl group of linear chain length one to six carbons, preferably $C_1$ to $C_3$, with the following structure preferred:

(21)

In a preferred embodiment the two carbon linker of at least one macrocycle connects two adjacent nitrogens within the larger ring to form a six membered piperazine ring: for example with a 1,2-ethyl linker.

In this embodiment n is an integer from 0 or 1 and $R^1$ is an alkyl group of linear chain length one to six carbons, preferably $C_1$ to $C_3$, with the following structure preferred:

(16)

In a further embodiment there are one of more macrocyclic rings of different type arranged around the aryl centre, Ar (Ar=1,2-phenyl, 1,3-phenyl, 1,4-phenyl, 1,3,5-phenyl).

In this embodiment the following structure is preferred:

(20)

Transition Metal Complexes

The transition metal complexes of the present invention comprise one or more transition metals and a ligand with one or more macrocyclic chelators. The complexes of the present invention are charged species having formulae of the type shown in non-limiting examples 24 and 25. The transition metal may have valence of +1, +2, +3, +4 or +5. In these cases a pharmaceutically acceptable anion would be present in sufficient quantity to provide electronic neutrality. Non-limiting examples of preferred transition metals include Fe, Mn, Co, Ni, Cu and Zn.

Preferred examples of the linking aryl unit comprise a 1,4-substituted phenyl unit, a 1,2-substituted phenyl unit, a 1,3-substituted phenyl unit or a 1,3,5-substituted phenyl unit. The most preferred substitution being 1,4-substituted phenyl. The remaining positions of the phenyl unit that are not substituted with macrocycles ($A_1$, $A_2$ or $A_3$) may be unsubstituted or alkyl substituted (linear alkyl chain $C_1$ to $C_3$) with methyl substitution preferred and unsubstituted most preferred.

Linkage to Fluorophore

Another embodiment of the present invention comprises the attachment of a fluorescent tag to one or more of the macrocyclic chelators either in the presence or absence of one or more transition metal ions. A non-limiting example of a pharmaceutically viable fluorescent tag is Rhodamine B.

Linkage to Radioisotope

Another embodiment of the present invention comprises of the insertion of one or more radioisotopes into one or more of the macrocyclic chelators either in the presence or absence of one or more transition metal ions. A non-limiting example of a pharmaceutically significant radioisotope for imaging applications is [64]Cu [following a similar procedure to that described by X. Sun et al. Journal of Medicinal Chemistry, 2002, 45, 469.]

Other Aspects

Another embodiment of the present invention relates to a method of treating viral disorders which comprises administering to a mammal an amount of a compound selected from Formulae 1, 2 or 3, effective for treating the disorder, optionally together with one or more excipients or pharmaceutical carriers.

Generally, a sterile aqueous solution or a physiological or buffered solution of the invention or of its metal complexes will be administered to the patient in a variety of ways, including orally, intrathecally and especially intravenously. The invention may also be co-administered with other pharmaceuticals for anti-viral treatment.

EXAMPLES

Example 1 para-Xylyl bis(1,5,8,12-tetraazabicyclo[10.2.2]hexadecane (Compound of Formula 16)

(16)

cis-Perhydrotetraazapyrene, 1.2 g (5.40 mmol) and para-xylenedibromide, 0.71 g (2.70 mmol) were stirred together in dry acetonitrile (20 ml) for 24 hr. A white precipitate resulted which was collected by filtration, washed in acetonitrile and dried in vacuo to give a white solid (1.35 g, 71%). [Procedure modified from M. Le Baccon et al, New Journal of Chemistry, 2001, 25, 118.] Mass and NMR ($^1$H and $^{13}$C) spectra were consistent with the expected product.

This compound, 1.16 g (1.60 mmol), was dissolved in dry ethanol (100 ml), stirred under nitrogen and NaBH$_4$, 0.61 g (16 mmol), added over a period of 20 mins. The solution was then stirred for a further 30 mins and refluxed under nitrogen for one hour. The solution was cooled to room temperature, 3M HCl (10 ml) was added slowly and the solvent removed. The resulting residue was dissolved in water (30 ml) and the pH was reduced to 14 using KOH pellets. Benzene was used to extract the basic solution (6×50 ml). The combined extracts were dried, filtered and the solvent removed giving a white solid, (0.59 g, 65%):

$^1$H NMR (400 MHz, CDCl$_3$) δ 7.20 (s, 4H, ArH), 3.65 (s, 4H, NCH$_2$Ar), 3.27 (m, 4H, NCH$_2$), 3.02 (m, 4H, NCH$_2$), 2.93 (m, 4H, NCH$_2$), 2.70 (m, 4H, NCH$_2$), 2.63 (m, 8H, NCH$_2$), 2.56 (m, 12H, NCH$_2$), 2.26 (m, 4H, NCH$_2$), 1.81 (s, 4H, NCH$_2$), 1.72 (m, 4H, NCH$_2$).

$^{13}$C NMR (CDCl$_3$) δ 136.40 (ArCH$_2$), 129.36 (ArH), 57.07 (ArCH$_2$N), 56.24 (CH$_2$N), 55.51 (CH$_2$N), 55.15 (CH$_2$N), 54.73 (CH$_2$N), 51.30 (CH$_2$N), 50.62 (CH$_2$N), 48.26 (CH$_2$N), 48.17 (CH$_2$N), 26.43 (NCH$_2$CH$_2$), 23.52 (NCH$_2$CH$_2$).

The HCl salt of this compound was formed by following method. The solid, 101 mg (0.19 mmol), was dissolved in methanol (10 ml) and conc HCl:methanol (1 ml:20 ml) was added dropwise until a precipitate was observed. Filtrate was decanted off and this process was repeated twice. Finally, the filtrate was concentrated in vacuo to give a white powder as product. Mass and NMR ($^1$H and $^{13}$C) spectra were consistent with the expected product.

Example 2

Formula 17 para-Xylyl bis(1,5,8,12-tetraazabicyclo[10.2.2]hexadecane (0.47 g/0.85 mmol) was dissolved in DCM (100 ml). K$_2$CO$_3$ (0.22 g/1.62 mmol) and methyl iodide (0.23 g/0.10 ml/1.62 mmol) were added and the mixture was stirred at room temperature under nitrogen overnight. The reaction mixture was filtered to remove K$_2$CO$_3$ and the filtrate was concentrated in vacuo to yield an orange solid. Mass and NMR (1H and 13C) spectra were consistent with the expected product. Yield=0.47 g (96%).

Example 3

Formula 21

Synthesis of para-xylyl bis(1-methyl-1,5,8,12-tetraazabicyclo[6.6.2]hexadecane

The bisaminal precursor, 0.41 g (5.82 mmol) was added to 15 ml of dry DMF and methyl iodide, 0.725 ml (12.0 mmol) then the solution was stirred for 14 days. The solvent was removed on the rotary evaporator giving a white solid, (0.38 g).

The white solid, 0.38 g (6.6 mmol) in minimum of dry ethanol was reduced with NaBH$_4$, 2.49 g (66 mmol). The NaBH$_4$ was added over a period of 1 hour.

The reaction was left to stir for a further 14 days at room temperature. Excess NaBH$_4$ was decomposed with slow addition of 3M HCl (10 ml) and the solvent removed. The resulting white solid was dissolved in water (30 ml), the pH was adjusted to 14 using KOH pellets, and the basic solution was extracted with benzene (6×50 ml).

The combined extracts were combined and the solvent removed, giving a yellow oil. Mass and NMR ($^1$H and $^{13}$C) spectra were consistent with the expected product.

Example 4

Metal Complexes Formulae 24 and 25

Ligand (112.4 mg/0.2 mmol) was dissolved in methanol (20 ml) and copper chloride (0.07 g/0.4 mmol) was added. The blue solution was refluxed for 2 hours and stirred at room temperature for 48 hours. The solution was concentrated in vacuo and redissolved in a minimum amount methanol for recrystallisation.

Ligand (133.6 mg/0.23 mmol) was dissolved in methanol (20 ml) and zinc acetate (0.10 g/0.46 mmol) was added. The orange solution was refluxed for 2 hours and stirred at room temperature for 48 hours. The solution was concentrated in vacuo and redissolved in a minimum amount methanol in an attempt to grow crystals.

Mass spectra and elemental analysis were consistent with the expected products.

Example 5

Unsymmetric Compounds (22)

Glyoxal bridged cyclam (4.97 g/22.39 mmol) was dissolved in dry THF (50 ml) and 4-(methylbromo)benzoic acid ester (5.14 g/22.39 mmol) was added. The resulting yellow solution was stirred at room temperature under nitrogen for 4 days. The filtrate was decanted off and washed with further THF (4×20 ml). The remaining precipitate was concentrated in vacuo to yield a white powder as product. Mass and NMR ($^1$H and $^{13}$C) spectra were consistent with the expected product.

One-armed macrocycle (4.93 g/10.91 mmol) was dissolved in methanol (250 ml) and cooled to 0° C. in an ice bath. NaBH$_4$ (3.80 g/100 mmol) was added slowly over 30 minutes. The solution was stirred at room temperature for 1 hour and concentrated in vacuo to a white solid as the product. Mass and NMR (1H and 13C) spectra were consistent with the expected product.

This compound (2.37 g/6.35 mmol) was dissolved in CH$_3$CN (50 ml) and K$_2$CO$_3$ (0.87 g/6.35 mmol) was added. Methyl iodide (0.90 g/0.40 ml/6.35 mmol) was added and the mixture was stirred at room temperature under nitrogen overnight. The resulting mixture was filtered to remove K$_2$CO$_3$ and concentrated in vacuo to yield an orange powder as product.

The one-armed ester (2.43 g/6.35 mmol) was dissolved in dry THF (100 ml) and BH$_3$.SMe$_2$ (2.06 ml/20.64 mmol) was added. The mixture was refluxed under nitrogen for 6 days The reaction was monitored by TLC to determine when it was complete. The reaction mixture was cooled in an ice bath and methanol was added until all the BH$_3$.SMe$_2$ had been consumed. The solution was concentrated in vacuo to yield a white solid. This was dissolved in brine (150 ml) and extracted with dichloromethane (2×150 ml, 1×300 ml). The combined extracts were collected, dried (MgSO$_4$) and concentrated in vacuo to yield a white solid. This was purified by column chromatography (95% DCM, 5% methanol and 3 drops of Et$_3$N).

Yield=0.93 g (40%) (% yield for steps 4 and 5 together is 37%). $^1$H NMR (CD$_2$Cl$_2$) δ 1.62-1.64 (m, 1H), 2.07 (s, 1H, CH$_2$OH), 2.40-2.79 (m, 6H), 3.28 (s, 5H), 3.61-3.66 (m, 2H), 3.88-3.89 (m, 3H), 4.60-4.70 (m, CH$_2$OH), 7.34-7.36 (m, 2H, CH$_{aromatic}$, J=8.16 Hz), 8.00-8.05 (m, 2H, CH$_{aromatic}$ J=8.16 Hz). $^{13}$C NMR (CD$_2$Cl$_2$) δ 1.10, 67.18, 67.19, 77.40, 77.72, 78.04, 129.67 (C$_{aromatic}$), 129.96 (CH$_{aromatic}$), 130.00 (CH$_{aromatic}$).

One-armed macrocycle alcohol (0.79 g/2.20 mmol) was added to PBr$_3$ (0.19 ml/2.20 mmol) and a catalytic amount of pyridine (~0.02 ml) was added. The mixture was stirred at room temperature overnight (an orange colour was observed) and at 100° C. for 1 hour. Water (20 ml) was added slowly and made up to pH 14 with KOH pellets. The aqueous layer was extracted with dichloromethane (3×30 ml). The combined extracts were collected, dried (MgSO4) and concentrated in vacuo to yield an orange solid as product. Yield=0.64 g (69%) $^1$H NMR (CD$_2$Cl$_2$, 400 MHz) δ: 7.19 (d, 8.2 Hz), 7.88 (d, 8.2 Hz), 3.17-3.00 (m, 2H), 2.97-2.83 (m, 2H), 2.82-2.68 (m, 2H), 2.60-2.18 (m, 16H), 2.15-2.02 (m, 2H), 1.72-1.50 (m, 6H).

(23)

One-armed bromide (0.30 g/0.71 mmol) was dissolved in CH$_3$CN (100 ml) and butanedine bridged cyclam (0.18 g/0.71 mmol) was added. The resulting dark orange solution was stirred at room temperature under nitrogen for 48 hours. The filtrate was decanted off and washed with further CH$_3$CN (4×20 ml). The remaining precipitate was concentrated in vacuo to yield a white/orange solid as product.

Yield=0.23 g (48%)

(20)

Bis-macrocycle with butanedione bridged pendent arm (11) (0.21 g/0.31 mmol) was dissolved in ethanol (50 ml) and HCl (10% aq./50 ml) was added. The orange solution was stirred at 60° C. for 48 hours. The solution was concentrated in vacuo and water (50 ml) was added. The pH was raised to 14 with KOH. The aqueous layer was extracted with DCM (3×100 ml). The combined extracts were collected, dried (MgSO$_4$) and concentrated in vacuo to yield a yellow oil.

Example 6
1,5,9,13-Tetraazabicyclo[11.2.2]heptadecane derivatives 1,1'-[1,4-phenylenebis (methylene)]-bis(1,5,9,12 Tetraazabicyclo[3.6.9.11]heptadecane)

The bis-monoquaternary macrocycle salt [synthesised by a modified procedure from M. Le Baccon et al, New Journal of Chemistry, 2001, 25, 118.] (1.27 mmol, 0.933 g) in dry ethanol (100 ml) was cooled in an ice bath under an inert atmosphere. Sodium borohydride (12.2 mmol, 0.479 g) was added slowly. The mixture was stirred for 30 minutes and refluxed for 1 hour. The solvent was evaporated and water (60 ml) added. The pH was then raised to 14 using KOH. Dichloromethane was used to extract the basic solution and the extracts were dried over sodium sulphate for 30 minutes. The solution was then filtered and the solvent removed from the filtrate to give a white solid. Mass and NMR ($^1$H and $^{13}$C) spectra were consistent with the expected product. Yield=91%.

Formation of the HCl Salt.

The bis(macrocycle) (0.3448 mmol, 0.2 g) was dissolved in ethanol (20 ml) and HCl gas was bubbled through the solution for 5 minutes. A white powder precipitated out and was filtered off to yield the HCl salt. Mass and NMR ($^1$H and $^{13}$C) spectra were consistent with the expected product. Yield=85%

Formation of a Copper Complex

Copper acetate (0.74 mmol, 0.158 g) in methanol (30 ml) was slowly added to stirred solution of the bis(macrocycle) (0.34 mmol, 0.20 g) in methanol (20 ml) under an inert atmosphere. The copper solution changed colour from turquoise to blue on addition to the macrocycle solution, indicating that the copper was complexing with the macrocycle. The mixture was stirred and refluxed for 1 hour. After which it was dried on the schlenk line to yield a blue crystalline powder. The mass spectrum was consistent with the expected product. Yield=0.29 g (90%)

Formation of the Zinc Complex

Zinc acetate (0.74 mmol, 0.159 g) in methanol (30 ml) was slowly added to stirred solution of the bis(macrocycle) (0.34 mmol, 0.20 g) in methanol (20 ml) under an inert atmosphere. The mixture was stirred and refluxed for 1 hour after which the product was dried on the schlenk line to yield the zinc complex. The mass spectrum was consistent with the expected product.

Example 7

Fluorophore Tagged CXCR4 Binding Molecules for Receptor Imaging

Formation of Rhodamine-Bridged Macrocycle Conjugate

The conjugate was formed following the typical procedure for combining an isothiocyanate with a free amine group to form a thiourea linkage [example methodology M. M. Hüber et al., Bioconjugate Chemistry, 1998, 9, 242.]. Equimolar amounts of rhodamine B isothiocyanate was combined with the one armed macrocycle containing a 4-aminobenzyl moiety and triethylamine in methanol and stirred at RT overnight. The product was purified by passing down a sephadex LH-20 column eluted with methanol. The NMR and mass spectral data were consistent with the desired conjugate.

Formation of Copper Complex

Equimolar amounts of copper perchlorate and rhodamine B-bridged macrocycle conjugate were combined in ethanol and heated to reflux for 2 h. On evaporation the complex was obtained as a purple solid that could be purified further by passing down a sephadex LH-20 plug in methanol.

Binding of Rhodamine-Bridged Macrocycle Conjugates and Complexes

Two monocyclam compounds were tagged with rhodamine and specific binding to the CXCR4 receptor was analysed by incubating with jurkat cells. Cell samples were analysed by flow cytometry as described in example 8, below.

Rhodamine-Bridged Macrocycle Conjugate Activity

Figure 1:
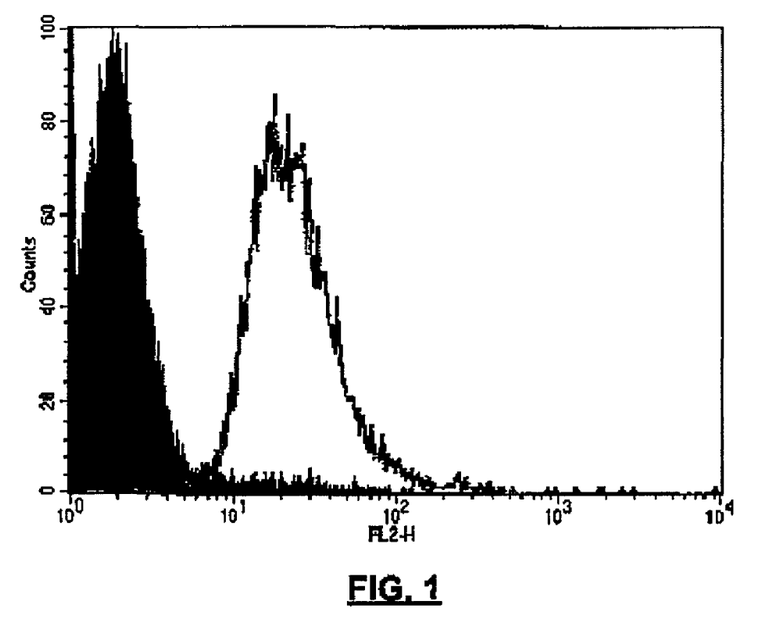
FIG. 1 is a histogram providing flow cell cytometry binding data for a rhodamine fluorophore conjugate molecule according to the present disclosure that shows binding of a chelator to a CXCR4 chemokine receptor.

The structure of a novel rhodamine fluorophore conjugate molecule is shown below. With particular reference to FIG. 1, a histogram provides flow cell cytometry binding data showing binding of the chelator to the CXCR4 chemokine receptor.

Rhodamine-Bridged Macrocycle Copper Complex

Figure 2:
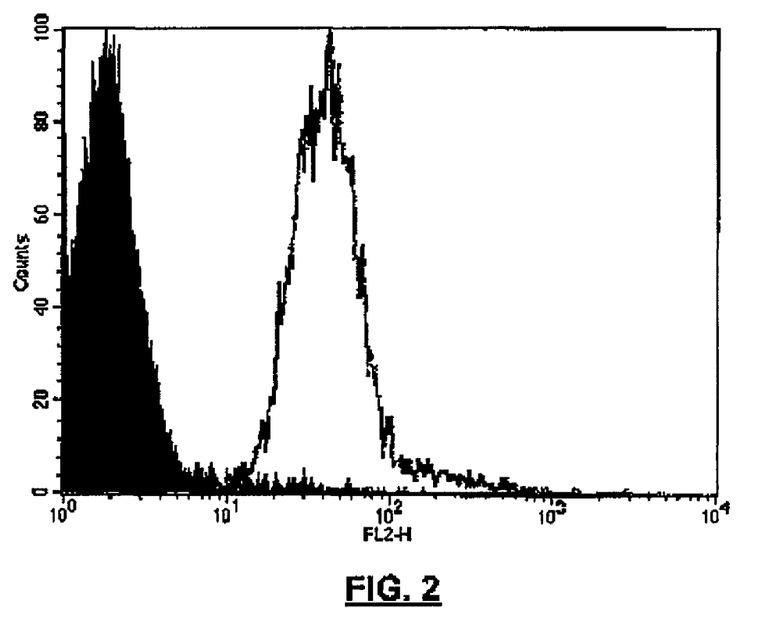
FIG. 2 is a histogram providing flow cell cytometry binding data for a rhodamine fluorophore conjugate molecule according to the present disclosure that shows binding of a copper complex to a CXCR4 chemokine receptor.

The structure of a novel rhodamine fluorophore conjugate molecule is shown below. With particular reference to FIG. 2, a histogram provides flow cell cytometry binding data showing binding of the copper complex to the CXCR4 chemokine receptor.

Example 8

Competition with CXCR4 Binding Antibodies Demonstrating CXCR4 Receptor Binding
Antibody Stainings and Flow Cytometry The antibodies used in this study were: unconjugated mouse anti-human CXCR4 mAbs clones 44708.111, 44716.111, PE-conjugated clone 44717.111 and 12G5 (R&D Systems Europe, Abingdon, UK). Cells were preincubated with 20 μM of the compound for 30 mins. Thereafter cells were incubated with each of the mAbs for a further 60 mins. In the case of the direct binding assay, serial dilutions of the compound were added simultaneously with the antibody (44708.111). Cells were then incubated with a secondary fluorescein isothiocyanate-conjugated anti-mouse antibody (IgG-FITC) (Serotec, UK) for 30 mins. Cell samples were analysed by a FACScan flow cytometer (BD Biosciences Europe. Erembodegem, Belgium). Data were acquired and analysed with CellQuest software (Becton Dickinson) on an Apple Macintosh computer. Relative percentage inhibitions were calculated from the mean fluorescent intensity of the whole cell population and relative inhibitory concentration (IC) values were obtained by non linear regression analyses using the Graphpad prism software.

The following table shows antibody competition studies that demonstrate our molecules effectively bind to the CXCR4 chemokine receptor and compete with CXCR4 specific monoclonal antibodies.

| Antagonist | IC50 (μM) | IC90 (μM) |
| --- | --- | --- |
| 25 | 0.178 | 0.853 |
| Zn(21) | 0.254 | 1.349 |
| 24 | 0.260 | 1.516 |
| Cu(16) | 0.331 | 2.845 |
| 16 | 17.025 | >17.025 |

Anti-Viral Inhibitory Action and Cytotoxicities of Examples of the Drugs
Antiviral Assay and Cytoxicity Assay

Anti-HIV activity and cytoxicity measurements in MT-4 cells were based on viability of cells that had been infected or not infected with HIV-1 (IIIB) and HIV-2 (ROD) ×4 strainsexposed to various concentrations of the test compound [following the procedure of S. Harada et al., Science, 1985, 229, 563]. The MT-4 cells were allowed to proliferate for 5 d after which time the number of viable cells was quantified by a tetrazolium-based colorimetric method [described by R. Pauwels et al., Journal of Virology Methods, 1988, 20, 309.]

This data demonstrates the in-vitro anti-HIV activity of some of our compounds showing inhibition of infection by the HIV virus in MT-4 cells.

| Compound | HIV strain | av IC50 (μM) | av CC50 (μM) |
| --- | --- | --- | --- |
| 16 | HIV-1 | 6.98 | >225 |
|  | HIV-2 | 23.2 | >225 |
| Cu(16) | HIV-1 | 0.028 | >150 |
|  | HIV-2 | 0.060 | >150 |
| 24 | HIV-1 | 0.0025 | 60.56 |
|  | HIV-2 | 0.0040 | 60.56 |

The invention claimed is:

1. A compound of formula 1 or 2,
$A_1$-Ph (1) or $A_1$-Ar-$A_2$ (2) wherein $A_1$ and $A_2$ are selected from formulae 4 and

(4)

(5)

or a salt whereof;
wherein Ar is selected from the group consisting of 1,2-phenyl, 1,3-phenyl and 1,4-phenyl optionally substituted with one or more methyl groups;
each n is independently an integer from 0 to 1;
m is 1;
Ph is phenyl optionally functionalised with groups $R^4$, wherein $R^4$ is selected from the group consisting of methyl, other $C_1$ to $C_4$ alkyl and fluorophores; and
$R^1$ is selected from the group consisting of H, Me and linear chain $C_2$-$C_4$ alkyl;
with the proviso that when Ph is unsubstituted phenyl in formula 1 and $A_1$ is formula 4, $R_1$ is not Me.

2. A compound as claimed in claim 1 wherein $A_1$ and $A_2$ are independently selected from a group consisting of the formulae 7 to 15,

(7)

(8)

(9)

(10)

(11)

(12)

(13)

(14)

(15)

3. A compound as claimed in claim 1 or 2 wherein R is H or Me.

4. A compound as claimed in claim 1 wherein $A_1$ and $A_2$ are different.

5. A compound as claimed in claim 1 complexed with a metal ion selected from transition metal elements and mixtures thereof.

6. A compound as claimed in claim 1 labeled with a radioactive metal species or a fluorescent tag.

7. A compound of formulae 16, 17, 18, 19, 21, or 22,

(16)

(17)

(18)

(19)

-continued (21)

(22)

8. A pharmaceutical composition comprising a compound as claimed in claim 1 and a pharmaceutically inert carrier.

9. A method for imaging chemokine receptors comprising:
contacting a cell expressing a chemokine receptor with a compound according to claim 1, wherein the compound is covalently bound, chelated, or coupled to a radioisotope; and
detecting the radioisotope.

10. A method of cellular or tissue imaging of the CXCR4 receptor comprising:
contacting a cell or tissue expressing a CXCR4 receptor with a compound according to claim 1, wherein the compound is covalently bound, chelated, or coupled to a fluorophore; and
detecting the fluorophore.

11. The method of claim 10, further comprising sorting the cell based on detection of the fluorophore.

* * * * *